United States Patent [19]

Prindle

[11] Patent Number: 4,738,664
[45] Date of Patent: Apr. 19, 1988

[54] PISTOL GRIP SYRINGE
[75] Inventor: Gordon E. Prindle, Schaumburg, Ill.
[73] Assignee: Ideal Instruments, Inc., Chicago, Ill.
[21] Appl. No.: 39,957
[22] Filed: Apr. 20, 1987
[51] Int. Cl.[4] ............................................. A61M 5/315
[52] U.S. Cl. .................................... 604/228; 604/232
[58] Field of Search ............... 604/208, 209, 210, 228, 604/224, 232, 234

[56] References Cited

U.S. PATENT DOCUMENTS 2,722,215  11/1955  Dahlgren ...................... 604/228 X
2,879,766  3/1959   Wilburn .
2,880,723  4/1959   Adams .
3,110,310  11/1963  Cislak .
3,517,668  6/1970   Brickson ............................ 604/209
4,281,653  8/1981   Barta et al. .
4,677,980  7/1987   Reilly et al. ..................... 604/228 X Primary Examiner—John D. Yasko
Attorney, Agent, or Firm—Ian C. McLeod

[57] ABSTRACT

A pistol grip syringe (10) with a removable fluid container (16) is described. A piston (18) in the container separates from a driving rod (19) when the container is removed from the collar (56). The container is removed from the collar by turning one-quarter turn or less to unlock ears 16a on the container from the collar. A wedge (58) holds the rod in position during dispensing and is unlocked to pull the piston rearward in the container. The container can be disposable and the unit is easily cleaned.

6 Claims, 3 Drawing Sheets

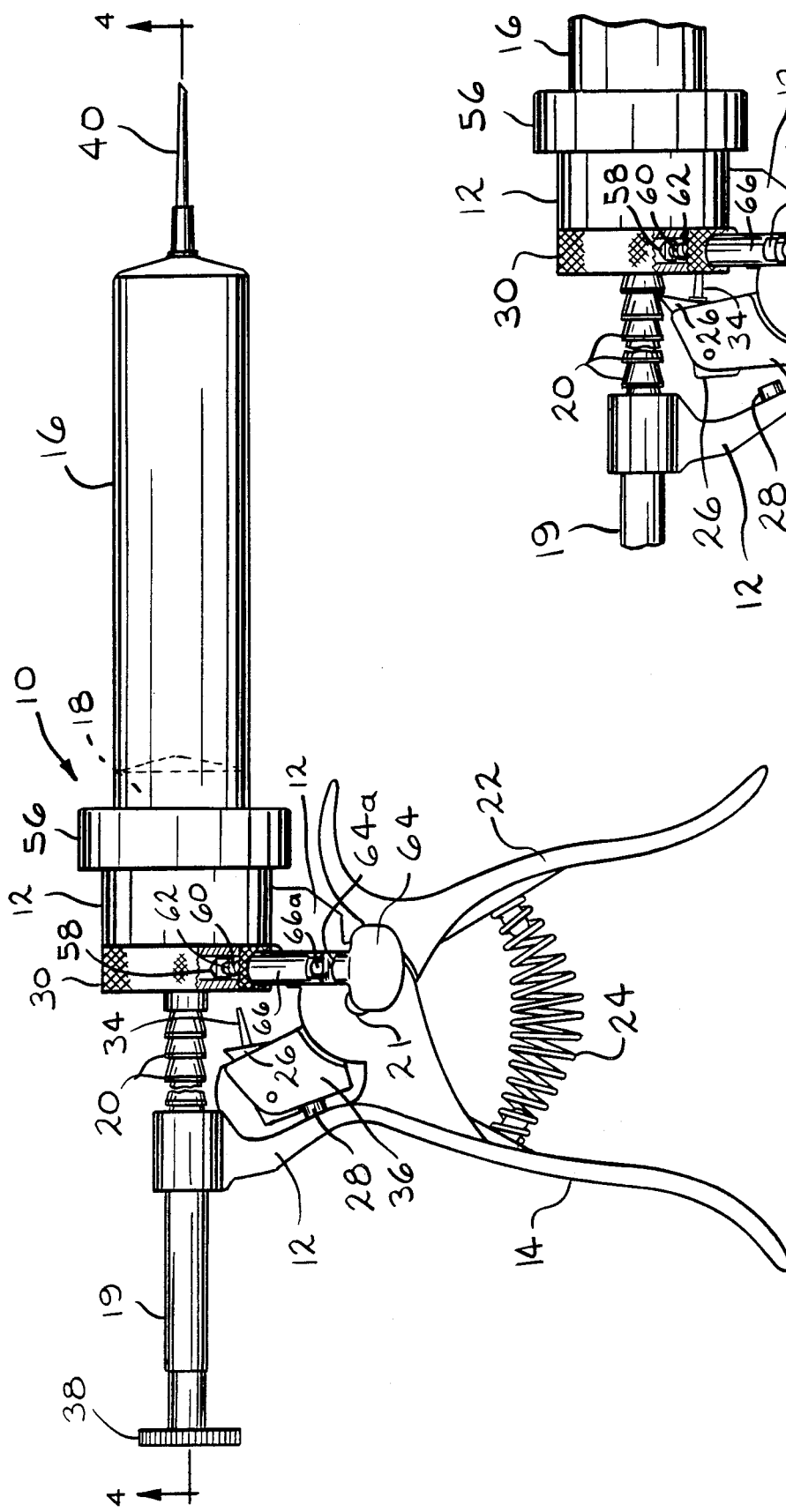
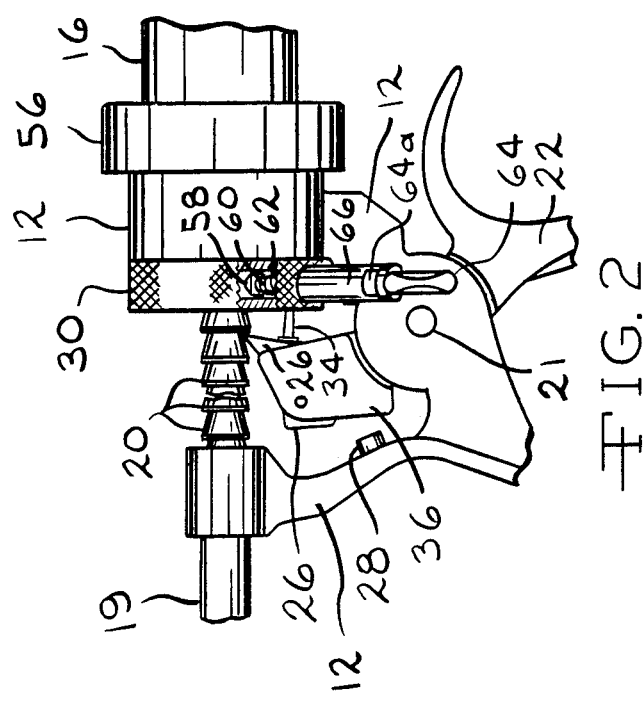

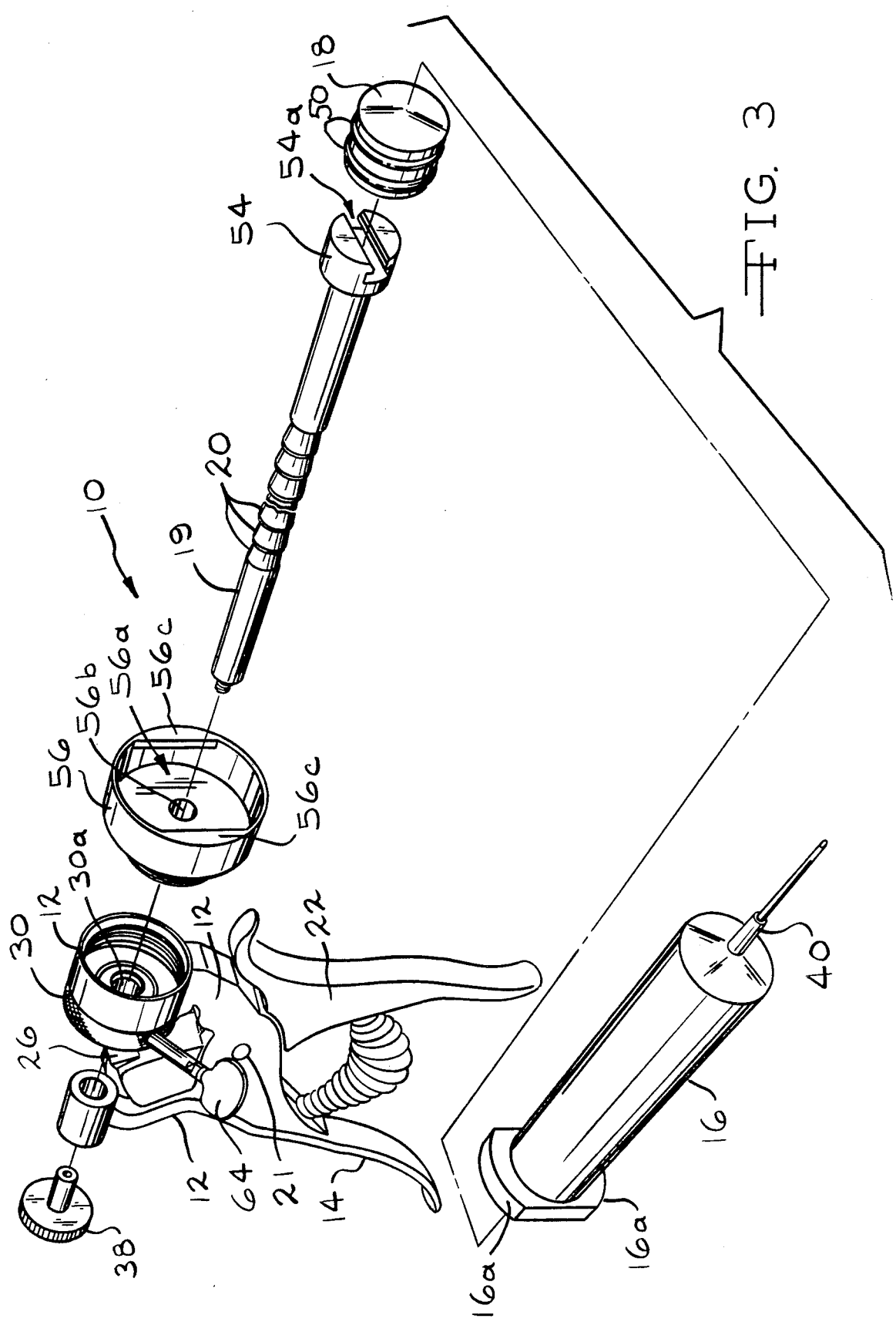

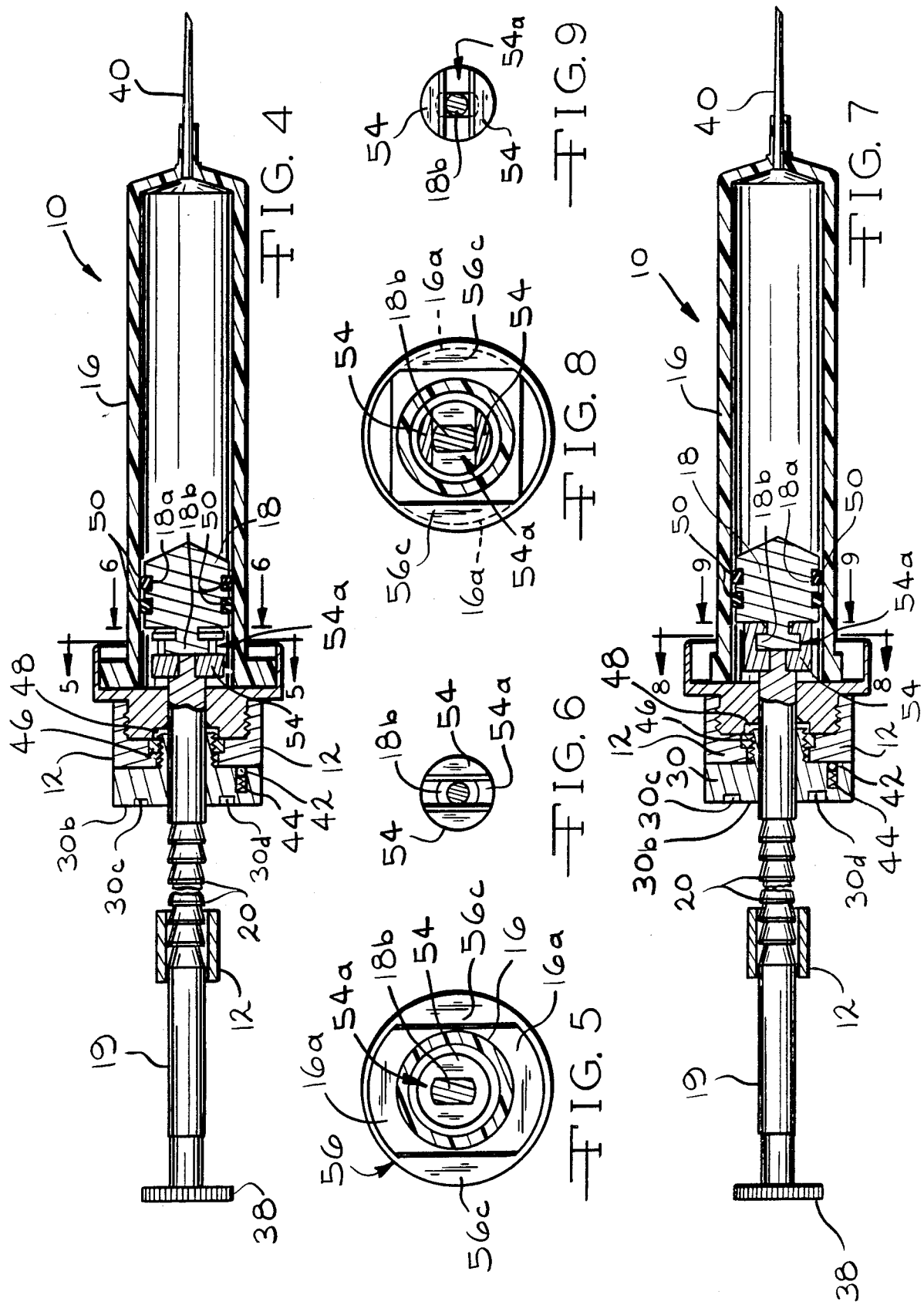

PISTOL GRIP SYRINGE

SUMMARY OF THE INVENTION

The present invention relates to an improved pistol grip syringe apparatus which has an easily removable container for the fluid to be dispensed from the syringe and a piston which easily disconnects from a driving rod of the apparatus with the container. In particular, the present invention relates to a syringe apparatus which allows the piston in the container to be connected with the driving rod by a one-quarter or less turn along with mounting the container on a frame of the apparatus by a one-quarter or less turn.

PRIOR ART

U.S. Pat. Nos. 2,879,766 to Wilburn; 2,880,723 to Adams and 4,281,653 to Barta et al describe syringes with a removable plunger connected to the piston. The plunger is threaded to the piston and the syringes are of the straight push plunger type.

U.S. Pat. No. 3,110,310 to Cislak shows a pistol grip metering syringe which uses a rack and pawl trigger activated mechanism for moving a driving rod connected to a piston. The metering is accomplished with a metering plate rotatable parallel to the axis of the driving rod which moves the piston. A related syringe apparatus uses a pin which engages recesses of varying depths in a plate which is rotated around the axis of the driving rod to position the recesses. In both instances the driving rod is threaded into the piston and is not intended to be removed except for repair of the syringe apparatus. The container is threaded into a frame of the apparatus. The problem with these syringes is that the container housing the piston is difficult to remove and clean and is not disposable.

OBJECTS

It is therefore an object of the present invention to provide a syringe apparatus with a container for the piston which can be disconnected by a quarter turn and which can be disposable. Further it is an object of the present invention to provide a syringe apparatus wherein the piston easily disconnects from the driving rod by a quarter or less turn. Further it is an object to provide an apparatus which is simple to construct and which is reliable. These and other objects will become increasingly apparent by reference to the following description and the drawings.

IN THE DRAWINGS

FIG. 1 is a front view of the preferred pistol grip metering syringe apparatus of the present invention particularly showing a locking wedge (58) in its unlocked position.

FIG. 2 is a front view in partial section showing the locking wedge (58) in its locked position between two teeth (20).

FIG. 3 is a separated perspective view of the syringe apparatus particularly showing the mounting of the container (16) on the collar (56) on the frame (12) prior to being twisted in the collar a one quarter or less turn to lock the container in position.

FIG. 4 is a front cross-sectional view along line 4—4 of FIG. 1 showing the container (16) in position in the collar (56) in the unlocked position.

FIG. 5 is an end cross-sectional view along line 5—5 of FIG. 4 showing the position of a T (18b) on a piston (18) in a slot (54a) of a connector (54).

FIG. 6 is an end cross-sectional view along line 6—6 of FIG. 4 showing another view of the connector (54) and slot (54a).

FIG. 7 is a front cross-sectional view along the same line as in FIG. 4 except that the container (16) is locked on the collar (56) by twisting one-quarter turn.

FIG. 8 is an end cross-sectional view along line 8—8 of FIG. 7 showing the T (18b) locked in position on the connector (54).

FIG. 9 is an end cross-sectional view along line 9—9 of FIG. 7 showing another view of the T (18b) locked into the connector (54).

GENERAL DESCRIPTION

The present invention relates to a pistol type syringe apparatus including a frame with a handle, a fluid holding container mounted forwardly on the frame for dispensing a fluid from the container, a piston mounted for reciprocal movement in the container, a rod mounted on the piston projecting rearwardly from the piston and reciprocally supported by the frame, the rod having a forward position and a rearward position relative to the frame, a portion of the rod having teeth which provide a rack, a trigger mounted on the frame, a pawl mounted on the trigger for engagement with the rack to move the rod to the forward position when the trigger is pulled the improvement which comprises:

a collar mounted forwardly on the frame for holding the container, wherein the collar has a slot which provides locking and unlocking of ears on the container in the slot by twisting the container about one-quarter turn or less on a longitudinal axis the same as a longitudinal axis of the rod; and a T-shaped extension and mating groove between the piston and the rod which engage such that the piston is locked onto the rod for reciprocal movement of the rod and piston together in the container when the container is twisted onto the collar with the rod in the rearward position and the piston is unlocked from the rod when the container is twisted and removed from the collar.

In particular the present invention relates to a multi-dose metering hypodermic syringe apparatus including a frame with a handle, a fluid holding cylinder mounted forwardly on the frame for dispensing a fluid from the cylinder, a piston mounted for reciprocal movement in the cylinder, a rod having a longitudinal axis connected to the piston projecting rearwardly from the piston and reciprocally supported by the frame, the rod having a rearward position and a forward position relative to the pawl, a portion of the rod having teeth to form a rack, a trigger pivotally mounted on the frame, including means for biasing the trigger and the handle apart, and a pawl pivotably mounted on the trigger for engagement with said rack to move the rod to the forward position when the trigger is pulled, and a metering member means for controlling the stroke length of the piston and the quantity of the dose the improvement which comprises:

a collar mounted on the frame around the rod and forward of the metering member for holding the cylinder wherein the collar has a slot which provides locking and unlocking ears on the cylinder in the slot by twisting the cylinder about one-quarter turn or less on a longitudinal axis the same as a longitudinal axis of the rod; and a T-shaped extension and mating groove between the piston and the rod which engage such that the piston is locked into the rod for reciprocal movement of the rod and piston together in the cylinder when the cylinder is twisted onto the collar with the rod in the rearward position and the piston unlocked from the rod when the cylinder is twisted and removed from the collar.

SPECIFIC DESCRIPTION

FIGS. 1 to 9 show the preferred multidose metering syringe apparatus 10 of the present invention. the apparatus includes a frame 12 with a handle 14, a fluid holding container or cylinder 16, preferably of clear plastic, a piston 18 in the cylinder 16, a rod 19 having teeth 20 which form a rack, a trigger 22 pivotably mounted on the frame on pin 21, and a spring 24 which biases the trigger 22 and handle 14 apart. A pawl 26 is mounted on the trigger 22 for engagement with the teeth 20 forming the rack. A pin 28 on the frame 12 lowers the pawl 26 when the trigger 22 is in the rest position. A spring (not shown) biases the pawl 26 into engagement with the teeth 20 when the pin 28 is disengaged from the pawl 26. A metering member 30 is rotatably mounted on the frame 12 concentric with the rod 18 and has an opening 30a (FIG. 3) through which the rod 19 passes. The metering member 30 has a surface 30b with cavities 30c and 30d (FIGS. 4 and 7) of varying depths circumferentially spaced around the rod 18. A projection 34 (FIGS. 1 and 2) is provided on the trigger 22 which moves to engage one of the cavities 30c or 30d. The projection 34 is fixed in position on the trigger 22. The depth of the cavity 30c or 30d limits the forward motion of the pawl 26. The pawl 26 pivots in a holder 36. A knob 38 is provided at one end of the rod 78 for pulling the rod 19 to a rearward position of the frame 12. A needle 40 is provided for using the syringe apparatus 10 for injections. It will be appreciated that the needle 40 is optional depending upon the dispensing needs. Referring to FIGS. 4 and 7 a ball 42 is mounted in metering member 30 and urged by a spring 44 into pockets (not shown) in the frame 12 for holding the metering member in a selected position. The metering member 30 is held onto frame 12 by nut 46 in recess 48. Essentially the unit as described is marketed by Ideal Instruments of Chicago, Ill. The metering member could also be in the form shown in the Cislak patent.

As shown in FIGS. 3 to 9, the piston 18 is provided with o-rings 50 in grooves 18a. The o-rings 50 tightly engage the inside wall of the container 16 so that the piston 18 is difficult to rotate in the container 16. The piston 18 is provided with a "T" end 18b which couples to a slot 54a in a connector 54. The container 16 has ears 16a and 16b which fit into a slot 56a in collar 56 with an opening 56b for the rod 18. The collar 56 is provided with lips 56c which engage the ears 16a and when the container 16 is twisted on collar 56. In FIGS. 4, 5 and 6 the "T" end 18b is inserted in slot 54a in connector 54 and ears 16a of container 16 are in slot 56a of collar 56. In FIGS. 7, 8 and 9 the ears 16a are rotated one-quarter turn in slot 56a and the end 18b turns one-quarter turn in slot 54a in connector 54. The rod 19 and piston 18 and the frame 12 and container 16 are then locked together. The o-rings 18a prevent the rotation of the piston 18 in the container 16 during the twisting.

It is preferred to provide a wedge 58 on pin 60 mounted perpendicular to the axis of the rod 19 as shown in FIGS. 1 and 2. A spring 62 urges the wedge 58 and pin 60 towards the rod 19. The wedge 58 engages the space between the teeth 20 forming the rack in the position shown in FIG. 2. The wedge 58 and pin 60 are lifted by pull 64 and twisted one-quarter turn as shown in FIG. 1 to disengage the wedge 58 from the rod 19. This allows the rod 19 to be moved rearwardly to pull the piston 18 to the rear of the container 16. For this operation, the pull 64 is lifted, pin 60 and wedge 58 are pulled against the spring 62 and twisted to lodge projection 64a of pull 64 out of slot 66a in tube 66. The wedge 58 does not interfere with the operation of the rod 19 when moved forward as shown in FIG. 2 because of the slant of the teeth 20.

In operation, when the piston 18 is in the most forward position in the container 16 it is reset into the dispensing position by pulling the wedge 58 from the teeth 20 by twisting the pull 64 to the position shown in FIG. 1. The rod 19 is then pulled rearward by knob 38 to reset the piston 18. By this movement the container 16 can then be refilled through the needle 40. The pull 64 is then reset as shown in FIG. 2 for dispensing using the trigger 22. When the container 16 and piston 18 are to be removed from the collar 56, the container is turned one-quarter turn from the position shown in FIG. 7 to the position shown in FIG. 4, preferably with the piston 18 in the most rearward position in the container 16. The piston 18 and rod 19 can then be separated with the piston 18 in the container 16 when the container 18 is removed from the collar 56. The piston 18 can be removed from the container 16 which can then be disposed of if it is made of a plastic material which is preferred.

It is intended that the foregoing description be only illustrative of the present invention and that the present invention be limited only by the hereinafter appended claims.

I claim:

1. In a pistol type syringe apparatus including a frame with a handle, a fluid holding container mounted forwardly on the frame for dispensing a fluid from the container, a piston mounted for reciprocal movement in the container, a rod mounted on the piston projecting rearwardly from the piston and reciprocally supported by the frame, the rod having a forward position and a rearward position relative to the frame, a portion of the rod having teeth which provide a rack, a trigger mounted on the frame, a pawl mounted on the trigger for engagement with the rack to move the rod to the forward position when the trigger is pulled the improvement which comprises:

(a) a collar mounted forwardly on the frame for holding the container, wherein the collar has a slot which provides locking and unlocking of ears on the container in the slot by twisting the container about one-quarter turn or less on a longitudinal axis the same as a longitudinal axis of the rod; and (b) a T-shaped extension and mating groove between the piston and the rod which engage such that the piston is locked onto the rod for reciprocal movement of the rod and piston together in the container when the container is twisted onto the collar with the rod in the rearward position and the piston is unlocked from the rod when the container is twisted and removed from the collar.

2. The syringe apparatus of claim 1 wherein the piston has a cylindrical cross-section and is provided with at least one resilient o-ring in a groove to sealingly and tightly engage the container which has a cylindrical cross-section mated to the piston so that the piston does not rotate in the cylinder when the cylinder is twisted onto the collar.

3. The syringe apparatus of claim 1 wherein a locking wedge is mounted on the apparatus to engage the rack so as to prevent the rod from moving to the rearward position in the container when dispensing the fluid and wherein the wedge is released from the rack to allow the rod to be moved to the rearward position to reset the piston in the container for further fluid dispensing.

4. In a multi-dose metering hypodermic syringe apparatus including a frame with a handle, a fluid holding cylinder mounted forwardly on the frame for dispensing a fluid from the cylinder, a piston mounted for reciprocal movement in the cylinder, a rod having a longitudinal axis connected to the piston projecting rearwardly from the piston and reciprocally supported by the frame, the rod having a rearward position and a forward position relative to the frame, a portion of the rod having teeth to form a rack, a trigger pivotally mounted on the frame, including means for biasing the trigger and the handle apart, and a pawl pivotally mounted on the trigger for engagement with said rack to move the rod to the forward position when the trigger is pulled, and a metering member means for controlling the stroke length of the piston and the quantity of the dose the improvement which comprises:

(a) a collar mounted on the frame around the rod and forward of the metering member for holding the cylinder wherein the collar has a slot which provides locking and unlocking ears on the cylinder in the slot by twisting the cylinder about one-quarter turn or less on a longitudinal axis the same as a longitudinal axis of the rod; and (b) a T-shaped extension and mating groove between the piston and the rod which engage such that the piston is locked into the rod for reciprocal movement of the rod and piston together in the cylinder when the cylinder is twisted onto the collar with the rod in the rearward position and the piston unlocked from the rod when the cylinder is twisted and removed from the collar.

5. The syringe apparatus of claim 4 is rotatably mounted on the frame concentric with the rod and having an opening through which the rod passes, the metering member including a surface defining cavities of varying depths circumferentially spaced around the rod, and a projection on the trigger fixed with respect to the pawl adapted to enter one of the cavities when the trigger is squeezed, whereby the depth of the particular cavity chosen limits the forward motion of the pawl and rack a predetermined distance for controlling the stroke length of the piston and wherein the metering member is provided with a locking wedge which engages the rack to prevent the rod from moving to the rearward position in the cylinder when dispensing the fluid and wherein the wedge is released from the teeth to allow the rod to be moved to the rearward position to reset the piston in the cylinder for further fluid dispensing.

6. The syringe apparatus of claim 5 wherein the locking wedge is mounted on a pin in the metering member perpendicular to the axis of the rod with a spring means on the pin which urges the wedge into engagement with the teeth and wherein the pin can be pulled away from the teeth to allow the rod to be moved to the rearward position and to reset the piston in the cylinder for further fluid dispensing.

* * * * *